United States Patent [19]

Feng

[11] Patent Number: 5,533,522

[45] Date of Patent: * Jul. 9, 1996

[54] METHOD OF AND ARRANGEMENT FOR OPTIMIZING DISEASE DIAGNOSIS

[76] Inventor: Genquan Feng, P.O. Box 1796, New York, N.Y. 10185-0016

[ * ] Notice: The portion of the term of this patent subsequent to Apr. 4, 2015, has been disclaimed.

[21] Appl. No.: 009

[22] Filed: Jan. 4, 1993

Related U.S. Application Data

[63] Continuation-in-part of Ser. No. 822,525, Jan. 17, 1992, abandoned, which is a continuation-in-part of Ser. No. 397,695, Oct. 30, 1989, abandoned, and Ser. No. 794,502, Nov. 19, 1991, abandoned.

[51] Int. Cl.$^6$ .............................. A61B 5/0476
[52] U.S. Cl. .............................. 128/731
[58] Field of Search .............................. 128/731

[56] References Cited

U.S. PATENT DOCUMENTS

| | | | |
|---|---|---|---|
| 3,489,287 | 3/1970 | Ertl | 128/731 |
| 3,809,069 | 5/1974 | Bennett | 128/731 |
| 4,279,258 | 7/1981 | John | 128/731 |
| 4,421,122 | 12/1983 | Duffy | 128/731 |
| 4,649,842 | 3/1987 | Raviv et al. | 128/731 |
| 4,932,416 | 6/1990 | Rosenfeld | 128/731 |

OTHER PUBLICATIONS

Liedtke et al, "International Journal of Biomedical Computing" vol. 8, No. 4, Oct. 1977, pp. 305–316, copy in 128/731.

Cohen et al, "Medical & Biological Engineering & Computing" vol. 15, Jul. 1977, pp. 431–437, copy in 128/731.

*Primary Examiner*—William E. Kamm

[57] ABSTRACT

Disease is non-invasively, accurately diagnosed at an early stage. A plurality of functions descriptive of the patient are mathematically determined. A set of indices for each function is established in advance. Each index has two states indicative of the patient's condition. An integrated pattern of the states of the indices from a plurality of the functions is generated and matched against a stored collection of index patterns whose diagnosis is known. The diagnosis is optimized with the aid of weighting factors for such parameters as patient's age and medical history.

2 Claims, 9 Drawing Sheets

METHOD OF AND ARRANGEMENT FOR OPTIMIZING DISEASE DIAGNOSIS

CROSS-REFERENCE TO RELATED APPLICATIONS

This application is a continuation-in-part of. U.S. patent application Ser. No. 07/822,525, filed Jan. 17, 1992, now abandoned. which, in turn, is a continuation-in-part of U.S. patent application Ser. No. 07/397,695, filed Oct. 30, 1989, now abandoned, and, in addition, is a continuation-in-part of U.S. patent application Ser. No. 07/794,502, filed Nov. 19, 1991, now abandoned.

BACKGROUND OF THE INVENTION

1. Field of the Invention

This invention generally relates to a method of, and an arrangement for, diagnosing a condition of a patient and, more particularly, to the diagnosis and the optimization of the diagnosis of disease in human patients.

2. Description of the Related Art

Heart and brain disease are still the leading causes of death around the world. Conventional detection of such disease relies on devices for measuring heart and brain wave activity by sensing electrical signals at various sites on the human body, and by recording these signals as waveforms. A cardiologist or a neurologist evaluates the waveforms to determine abnormalities therein. Such evaluation requires considerable training and skill. Even despite a high degree of training and skill, an waveform can still be interpreted as indicating normal activity even in the presence of advanced coronary artery disease and brain epilepsy. Experience has shown that conventional devices, although useful, are not sufficiently reliable to diagnose disease, either due to insufficient sensitivity or specificity, and certainly not at an early stage of disease. It has been estimated that over 50% of people with occlusive coronary artery disease or brain epilepsy have been reported to have normal EKG/EEG wave forms.

The prior art has proposed several approaches to extract more information from the signals.

However, in each case, usually a small portion of one cycle of the processed signal has been utilized. This has proven to be an unreliable diagnostic tool.

Signals arise from the discharge of electrical potentials from hundreds of thousands of electrically active cells, thereby resulting in a complex resultant signal. Isolated signal processing analysis of small portions of the processed signal does not produce reliable data. The analysis of a single function characteristic of the signal simply does not produce sufficient or reliable information. Conventional time and frequency domain analysis of the signal, as well as the analysis of isolated minor portions of single functions of the signal, fail to address information regarding non-linearities as well as cross correlation, coherence and phase angle over time. The joint effect of all these functions, particularly over an extended test period of many test cycles, has not been considered. As a result, the early and reliable detection of disease, as well as the specific diagnosis of the type of heart disease, are not presently available, particularly at a time when the chronic disease might be treated and its progress retarded or halted.

SUMMARY OF THE INVENTION

1. Objects of the Invention

It is a general object of this invention to advance the state of the diagnostic art for detecting disease.

Another object of this invention is to detect disease at an early stage in its progress.

Still another object of this invention is to non-invasively and accurately diagnose disease.

A further object of this invention is to diagnose different types of brain disease.

Another object of this invention is to optimize the diagnosis of different types of brain disease.

Yet another object of this invention is for remotely diagnosing the patient.

2. Features of the Invention

In keeping with these objects and others, which will become apparent hereinafter, one feature of this invention relates, in its broadest aspect, to determining a condition of a sample by acquiring electrical analog signals from the sample.

The method and arrangement of this invention, however, are not intended to be limited to the determination of heart disease from EKG signals, This invention can be extended to the analysis of any biological signals generated during the course of such medical examinations as an electromyogram, electrocephalogram electrobasogram, electrocorticogram, electrocystogram, electrogastrogram, electrometrogram, electronystagmogram, electro-oculogram, electroretinogram, electrospinogram, etc. In addition, the method and arrangement of this invention can be extended to the analysis of non-biological signals, e.g. physical signals or chemical signals, obtained during the course of measurement in a seismogram, eletrophoretogram, thermogram, etc.

This invention processes the analog signals, whether biological or not, and mathematically determines a plurality of functions descriptive of the sample being analyzed. Thus, in the case of EKG signals, the functions include, as described in detail below, the power spectrum characteristic, the coherence characteristic, the phase angle characteristic, the impulse response characteristic, the cross correlation characteristic and the amplitude histogram characteristic. Each of these functions carries a wealth of different information about the EKG signals, particularly when the functions are processed over an extended time period which, in the preferred embodiment, is 15 cycles lasting 10 seconds per cycle. The extended time period is many orders of magnitude greater than the typical analysis of EKG signals which, at best, process a minor fraction of one heart cycle of a heart function characteristic.

In accordance with this invention, a set of indices is established for each function. Each index has two states. The positive state indicates an abnormal condition for the sample. A negative state indicates a normal condition. The indices generally relate to the pattern or shape of the waveform of each function characteristic. As described in detail below, the preset indices include the magnitude of peaks, the intervals between peaks, the curvature of the peaks, the number of bends, etc.

An integrated index pattern of the states of the indices derived from a plurality, if not all, of the functions is generated. This integrated pattern is then matched against a stored collection of index patterns whose condition (i.e., diagnosis) is known. The best match then determines the diagnosis for the patient being analyzed.

The collection of stored index patterns is based on storing the index patterns of a multitude, e.g., many thousands, of patients whose condition is known and whose condition was confirmed by medical examination and testing. Thus, patients having myocarditis, for example, have index patterns which, when grouped together, have a distinctive pattern. Patients having a different heart disease have differently distinctive index patterns. As previously mentioned, the index pattern of the patient being tested is compared to each group of known patterns to find the best match and, hence, the diagnosis.

In the case of a cardiac patient, the collection of stored index patterns are advantageously grouped into the following eight categories: coronary heart disease, rheumatic heart disease, pulmonary heart disease, congenital heart disease, myocarditis, myocardiopathy, fibrillation and ventricle hypertrophy. This invention thus can match the cardiac patient's measured pattern against the patterns of these categories to select the one that best describes the patient's cardiac condition.

The number of matching indices compared to the total number of indices in the integrated index pattern is determined and, when multiplied by 100% is called the "score" or "raw score". In the preferred embodiment, the two categories of heart disease having the two highest scores are presented to the physician for suggested use in deciding upon the final diagnosis.

Prior to presentation of suggested diagnoses to the physician, various weighting factors are used to optimize the suggested diagnoses. For example, in the aforementioned case of a cardiac patient, the patient's age is a contributing factor and, hence, is used to modify the raw scores to achieve so-called "weighted scores" for presentation to the physician.

Factors, other than age, can be used. For example, the patient's known medical history is a significant parameter.

Hence, rather than relying on data extracted over a limited time for a single function, this invention relies on data extracted over an extended time from a plurality of functions, some of which have not heretofore been used in the diagnosis of disease.

The novel features which are considered as characteristic of the invention are set forth in particular in the appended claims. The invention itself, however, both as to its construction and its method of operation, together with additional objects and advantages thereof, best will be understood from the following description of specific embodiments.

DETAILED DESCRIPTION OF THE PREFERRED EMBODIMENTS

Referring now to the drawings, reference numeral 10 generally identifies an arrangement for diagnosing heart/brain disease in accordance with the method of this invention. Arrangement 10 includes a keyboard 12 for manual data entry and operational control, a monitor 14 for displaying and plotting data and a printer 16 for printing a written data record. As described below, electronic circuitry within the arrangement is employed to process EKG or EEG signals inn order to obtain a diagnosis of a condition of a patient 18.

Figure 3:
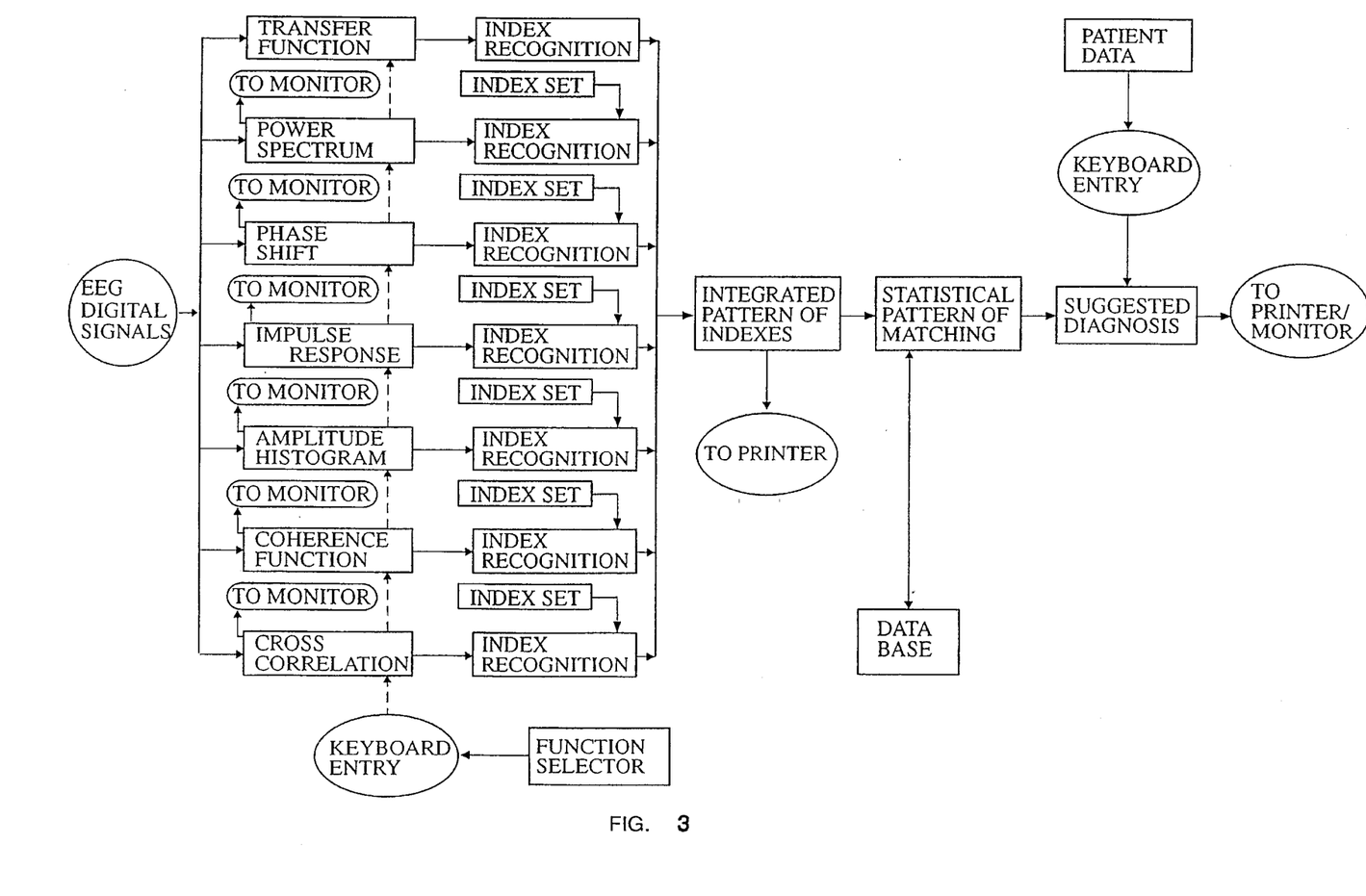
FIG. 3 is a block diagram of the EEG signal processor in FIG. 2.

An overview of the signal processing is depicted in FIG. 3. The digital EEG signals are fed to function blocks 43, 44, 46, 48, 50, 52 and 54 wherein the power spectrum, phase angle, impulse response, amplitude histogram, coherence and cross-correlation are respectively mathematically determined. In a preferred embodiment, all of these functions are determined and used in making the diagnosis. However, it is sufficient if at least two of these functions are determined. The choice of function to be determined at any particular time is selected by a function selector 56 which advantageously is a function key on the keyboard 12. Once mathematically determined, any particular function can be displayed as an analog waveform on the monitor 14.

Figure 5:
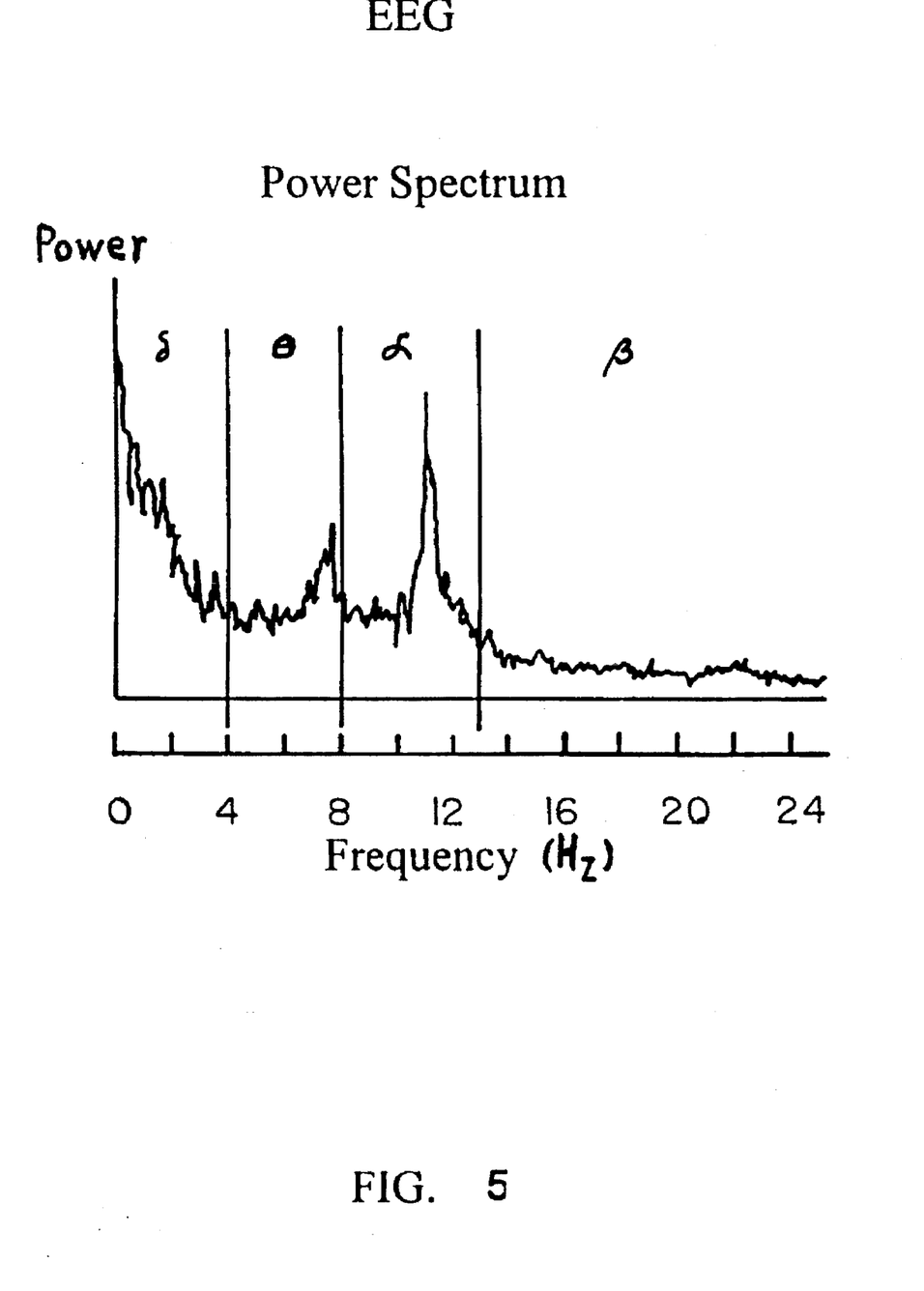
FIG. 5 is a power spectrum characteristic for the EEG signal of FIG. 4.
Figure 6:
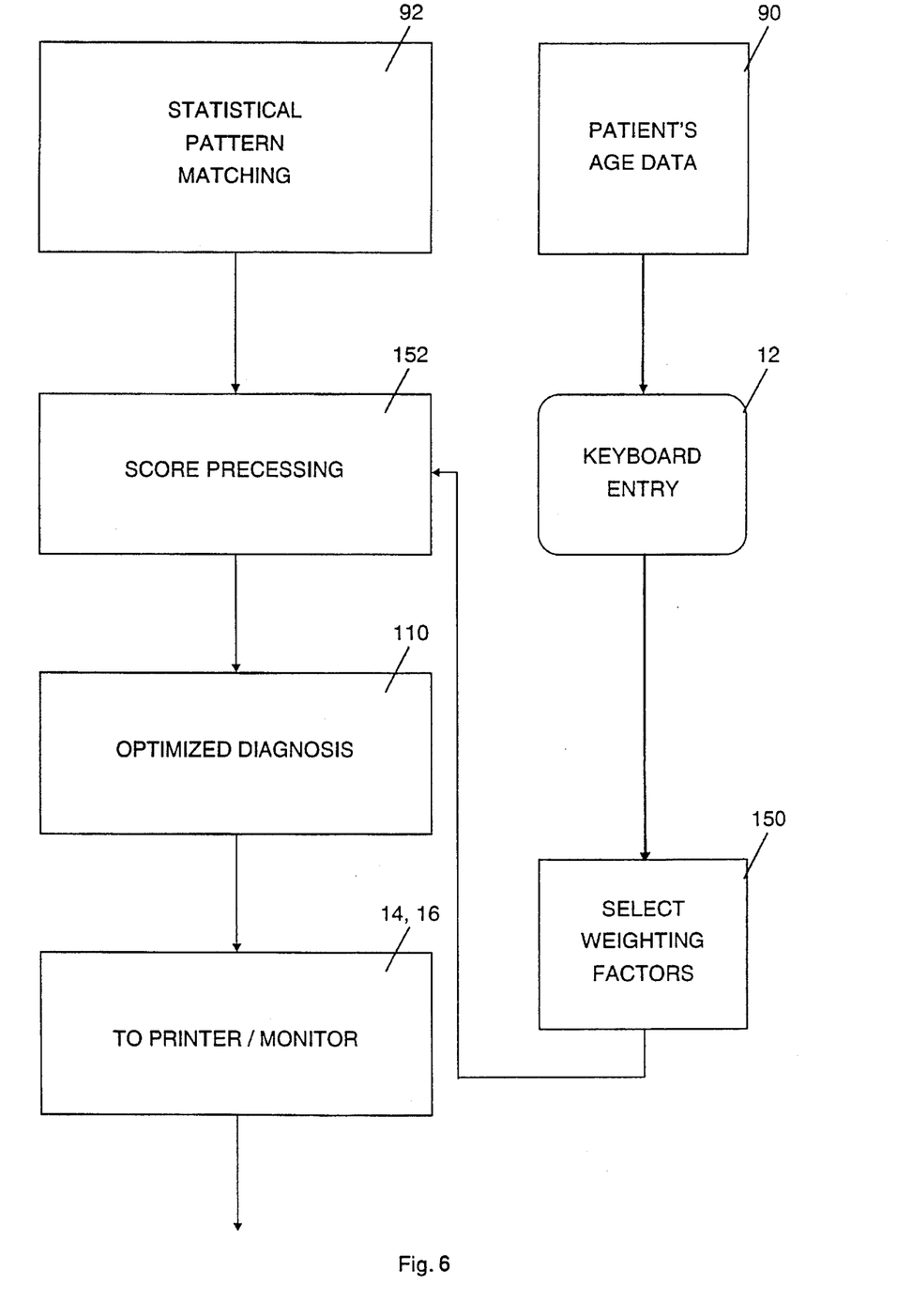
FIG. 6 is a flow chart depicting an improvement in the signal processor of FIG. 2.

The power spectrum function 44 is calculated as follows: The auto power spectrum $G_{xx}(f)$ for lead V5 is determined from equation (1):

$$G_{xx}(f)=S_x(f) \cdot S_x(f)^* \quad (1)$$

where $S_x(f)$ is the Fourier transform of the time-dependent, lead V5 signal $f_x(t)$ depicted in FIG. 5, and where $S_x(f)^*$ is the complex conjugate. The power spectrum $G_{xx}(f)$ for a patient under test is depicted in FIG. 6 wherein power is plotted against frequency.

Figure 7:
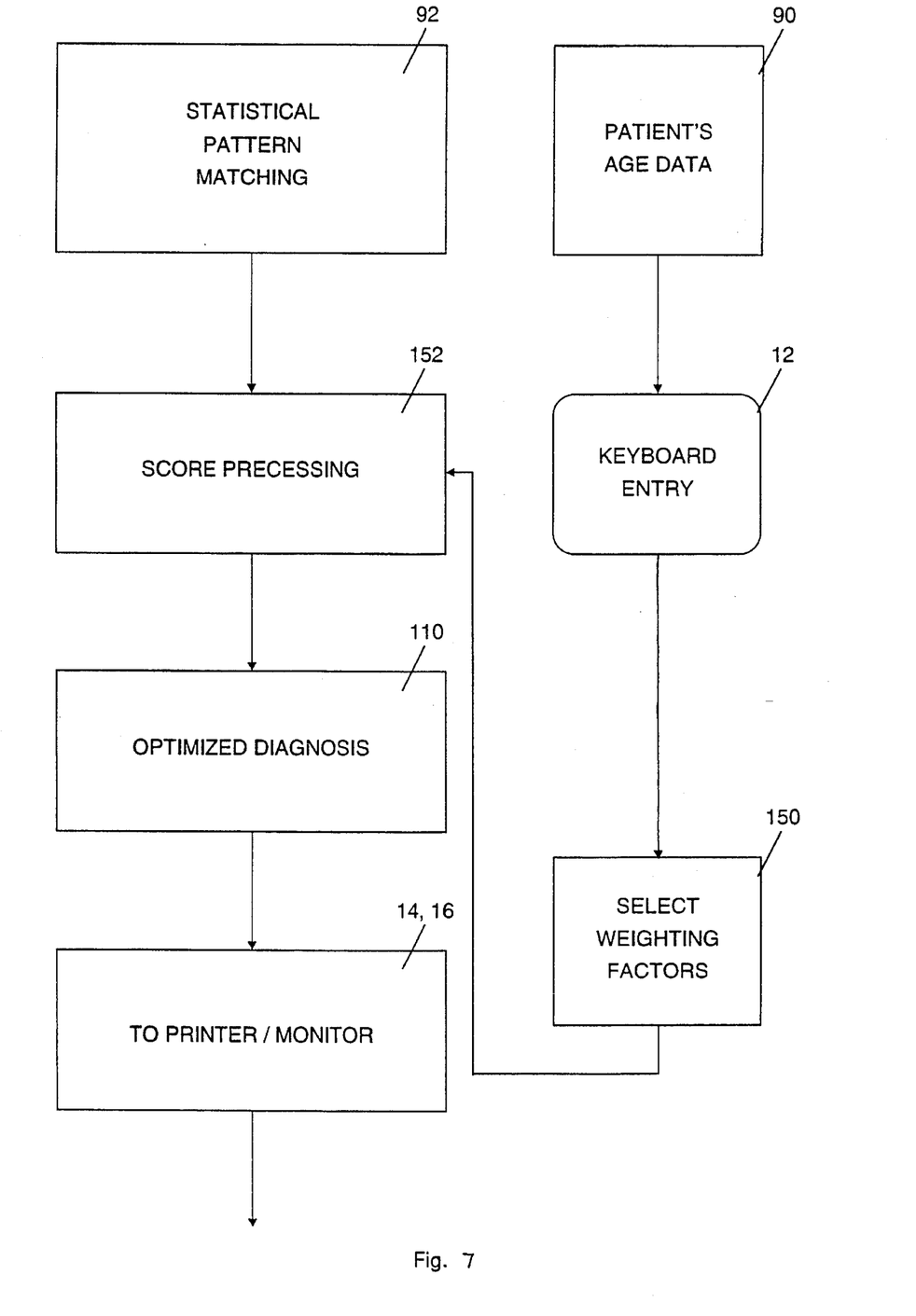
FIG. 7 is a flow chart depicting another improvement in the signal processor of FIG. 2.

The auto power spectrum $G_{yy}(f)$ for lead II is determined from equation (2):

$$G_{yy}(f)=S_y(f) \cdot S_y(f)^* \quad (2)$$

where $S_y(f)$ is the Fourier transform of the time-dependent, lead II signal $f_y(t)$, and where $S_y(f)^*$ is the complex conjugate. The power spectrum $G_{yy}(f)$ for a patient under test is depicted in FIG. 7 wherein power is plotted against frequency.

The phase angle function 46 is calculated as follows: First, the amplitude ratio of the transfer function $H_{xy}(f)$ is determined from equation (3):

$$H_{xy}(f)=G_{xy}(f)/G_{xx}(f) \quad (3)$$

where the cross power spectrum $$G_{xy}(f)=S_x(f) \cdot S_y(f)^* \quad (4)$$

and where $G_{xx}(f)$ is obtained in equation (1).

Second, the phase angle $\theta_{xy}(f)$ of the transfer function $H_{xy}(f)$ is determined from equation (5):

$$\theta_{xy}(f)=\tan^{-1}\{[IM(H_{xy}(f))]/[RE(H_{xy}(f))]\} \quad (5)$$

where IM and RE are the real and imaginary parts of the transfer function.

Figure 8:
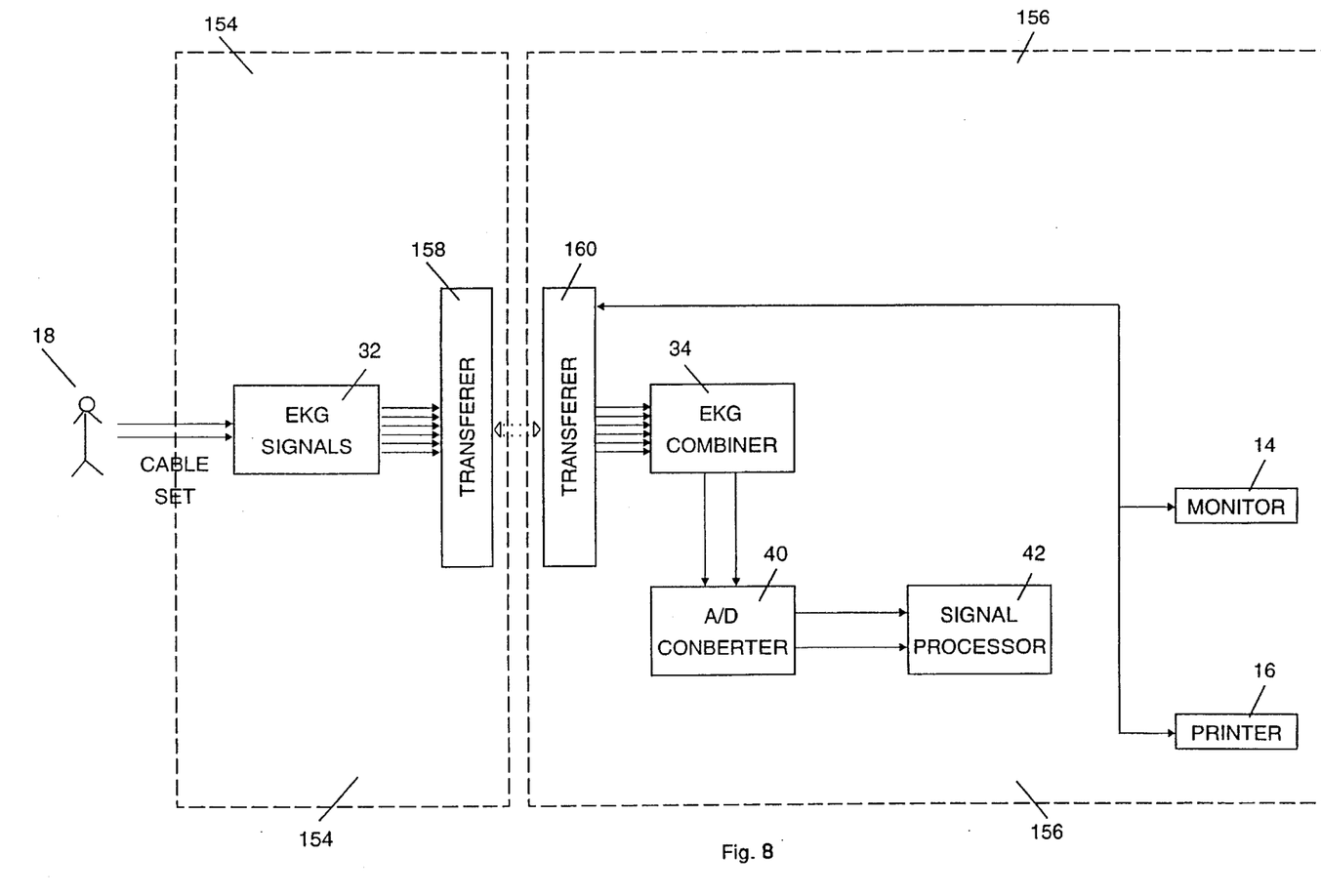
FIG. 8 is a block diagram depicting a remote signal processor system.

The phase angle is a measure of the time difference between the left ventricular (lead V5) and whole heart signals (lead II) and is depicted in FIG. 8 wherein phase in degrees is plotted against frequency. Phase leads and lags are respectively indicated above and below the reference line.

The impulse response function 48 is calculated as follows: The impulse response $IH_x(f)$ is determined from equation (6):

$$IH_x(f)=F^{-1}H_{xy}(f) \quad (6)$$

where $F^{-1}$ is the inverse Fourier transform of the transfer function $H_{xy}(f)$ defined in equation (3).

Figure 9:
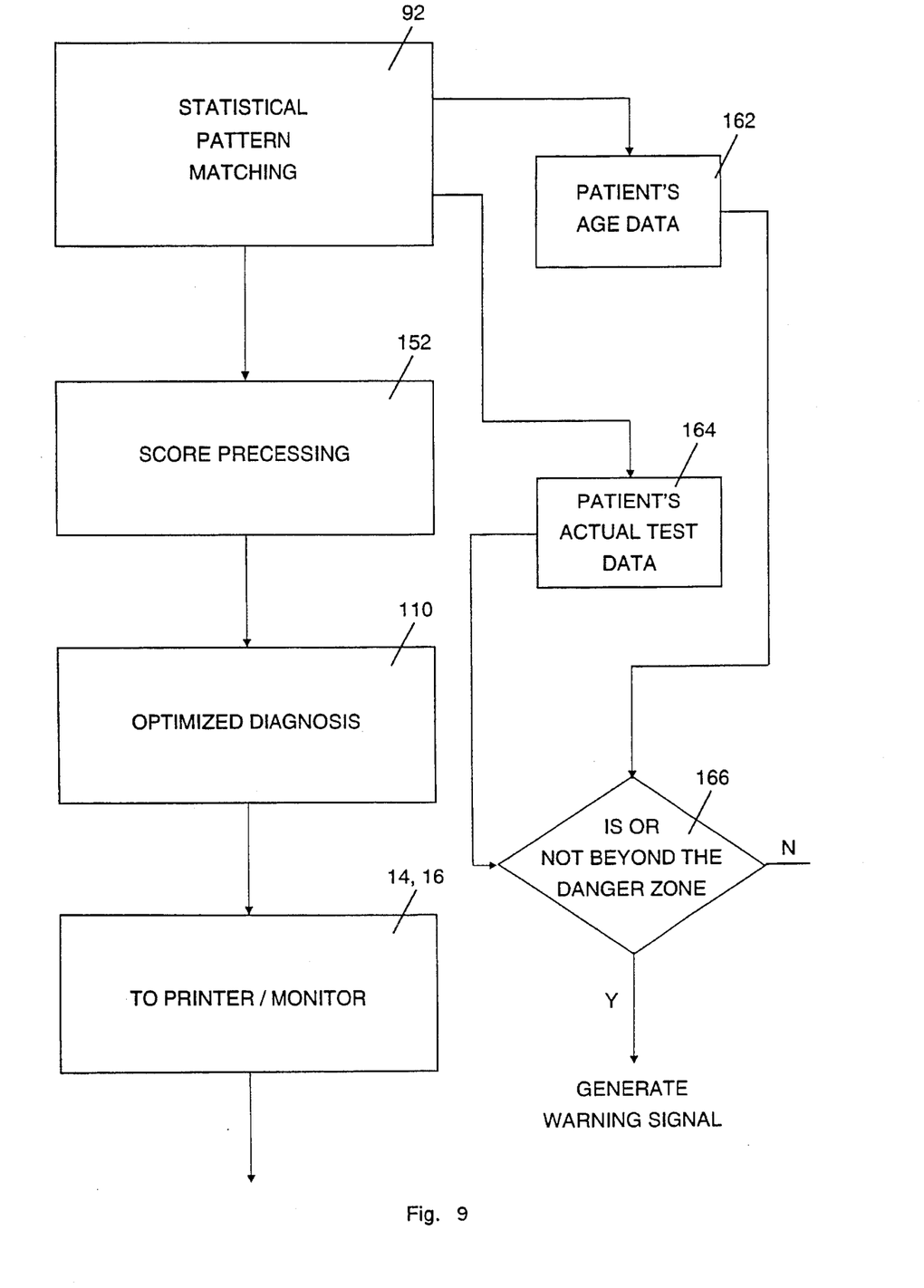
FIG. 9 is a flow chart depicting part of the operation of the system of FIG. 8.

The impulse response is a measure of the output response of the heart (lead II) solely in response to the input of the left ventricular signal (lead V5) and is depicted in FIG. 9 wherein amplitude is plotted against impulse time.

The amplitude histogram function 50 is a standard statistical analysis of the amplitudes present in the left ventricular (lead V5) and whole heart signals (lead II) and are respectively depicted in FIGS. 10 and 11 wherein the occurrence frequency is plotted against specific amplitudes. These plots indicate how many times a given amplitude is present in the left ventricular (lead V5) and whole heart signals (lead II).

The coherence function 52 is calculated as follows: The coherence $\alpha_{xy}(f)$ is determined from equation (7):

$$\alpha_{xy}(f)=G_{xy}(f)/G_{xx}(f)\cdot G_{yy}(f) \quad (7)$$

where $G_{xy}(f)$, $G_{xx}(f)$ and $G_{yy}(f)$ are defined in equations (4), (1) and (2). The coherence is depicted in FIG. 12 wherein coherence is plotted against frequency, The cross correlation function 54 is calculated as follows: The cross correlation $\phi_{xy}(\tau)$ is determined from equation (8):

$$\phi_{xy}(\tau)=\lim_{t\to\infty} \frac{1}{T}\int_0^\infty f_x(t)\cdot f_y(t+\tau)dt \quad (8)$$

where $f_x(t)$ and $f_y(t)$ are the left ventricular (lead V5) and whole heart signals (lead II), where $\tau$ is the delay time between the signals, and where T is the test period, typically 150 seconds. The cross correlation is a measure of the correspondence of the signals wherein cross correlation is plotted against the delay time.

Returning to FIG. 3, after the functions 43–54 have been calculated, they may be sequentially displayed on the monitor for evaluation by a technician, or, preferably, the function waveforms, are stored in a random access memory and subjected to a battery of tests in which the presence or absence of various indices are recognized. These indices all relate to the overall shape of the various function waveforms and are established in advance. Each function has its own individual pre-set indices as represented by blocks 58–88 in FIG. 3. Each of these indices has two states. A positive state indicates an abnormal condition. A negative state indicates a normal condition. The recognition of the indices occurs in a pattern recognition program as represented by blocks 70–80. The pre-set indices are set forth below for each function for an EEG analysis:

(I) Power Spectrum (1) ½—Is the amplitude ratio of the first peak/second peak above a limit?
(2) O—Is shape of any of first four peaks rounded similar to omega (Ω)?
(3) U1—Do any of first four peaks have a twinned peak?
(4) U2—Are the intervals between any of first four peaks unequal?
(5) U3—Is the inequality of the intervals between any of the first four peaks above a limit?
(6) U3xy—Same as U3 but are any two peaks simultaneously positive?
(7) U4—Is the shape of any peak similar to a hill (⌒)?
(8) U5—Is the shape of any peak similar to a mountain (⌒⌒)?
(9) N1—Is the first peak null?
(10) N3—Is the third and/or fourth peak null?
(11) S—Is the heart rate below 60 beats per minute?
(12) SS—Is the heart rate below 50 beats per minute?
(13) F—Is the heart rate over 100 beats per minute?
(14) FF—Is the heart rate above 120 beats per minute ?
(15) A1—Is the amplitude of the first peak above a limit?
(16) A2—Is the amplitude of any two of the first four peaks above a limit?
(17) A3—Is the amplitude of the second peak above a limit?
(18) A4—Is the amplitude of the third and/or fourth peak above a limit?
(19) A5—Is any one of the 5th–12th peaks higher than the first peak?
(20) A55—Are any two of the 5th–12th peaks higher than the first peak?
(21) A6—Are more than two of the 5th–12th peaks higher than the first peak?
(22) Nn—Are the first and second peaks higher than the third and fourth peaks?
(23) nN—Are the third and fourth peaks higher than the first and second peaks?
(24) Nnn—Is the first peak higher than the second, third and fourth peaks?
(25) nnN—Is the first peak lower than the second, third and fourth peaks?

(III) Impulse response (38) D1—Does the waveform have a double top plane wave resembling ⊐ or ⊓⊔⊓⊔?
(39) D2—Does the waveform have a stair steps wave resembling ⊐⌐?
(40) f—Is the main response impulse negative?
(41) M1—Does the main response impulse have a twin peak?
(42) M2—Does the shape of the main response impulse resemble the letter "M"?
(43) M3—Does the main response impulse have more than three peaks?
(44) M4—Does the main response impulse have a peak that is too wide?
(45) M5—Does the side response have a peak whose amplitude is above a limit?
(46) M6—Is the main response impulse totally downward?

(IV) Coherence (47) Q1—Is the coherence of the first peak of the power spectrum below a limit?
(48) Q2—Is the coherence of the highest peak of the transfer function below a limit?

(V) Amplitude Histogram (49) V+—Is the amplitude Of lead V5 above a limit?
(50) 2+—Is the amplitude of lead II above a limit?
(51) V—Is the amplitude of lead V5 below a limit?
(52) 2—Is the amplitude of lead II below a limit?
(53) Vn+—Is the number of bundles of the column in the amplitude histogram of lead V5 above a limit?
(54) Vn—Is the number of bundles of the column in the amplitude histogram of lead V5 below a limit?
(55) 2n+—Is the number of bundles of the column in the amplitude histogram of lead II above a limit?
(56) 2n—Is the number of bundkes of the column in the amplitude histogram of lead II below a limit?

(VI) Cross Correlation (57) RRR—Is the amplitude of the main peak above a limit?
(58) rrr—Is the amplitude of the main peak below a limit?
(59) R—Is the main peak within a higher zone?
(60) r—Is the main peak within a lower zone?
(61) RR—Is the interval betwee R1 and R2 above a limit?
(62) rr—Is the interval between R1 and R2 too short?
(63) rR—Is the peak R1 lower than the peak R2?
(64) R2—Is the peak R2 below a limit?
(65) R+—Does the peak R1 shift to the right side?
(66) R−—Does the peak R2 shift to the left side?
(67) Rw+—Is the bottom of the first positive peak below the bottom of the first negative peak, and so on for successive peaks?
(68) Rw−—Is the bottom of the first positive peak above the bottom of the first negative peak, and so on for successive peaks?
(69) pt—Is the number of peaks whose amplitude is above a threshold between peaks R1 and R2 above a limit?
(70) PT—Is there one or more peaks between peaks R1 and R2 higher than peak R2 above a limit?
(71) Rn—Does R2 have a twin peak or a zigzag shape?
(72) Rm—Is the peak R1 too wide?
(73) Rv—Is one bend of R1 too steep in slope?

Once the state of each index has been recognized, an integrated pattern 82 is generated. The integrated pattern contains the states of the indices from at least two, if not all, the above functions. The integrated pattern 82 can be printed out by the printer.

The printout is subdivided into three parts. A first part 84 contains patient data 90 entered via the keyboard 12. A second part 86 contains the aforementioned six functions together with the individual index legends and the results (+) or (−) of the index recognition. Some of the indices as set forth above have been deleted from FIG. 14 for ease of illustration. A third part 88 sets forth the diagnosis which is produced as described below.

Once the integrated pattern 82 is generated, it is fed into a statistical pattern matching program 92 to which a massive data bank is connected. The data bank includes a multitude of index patterns taken from thousands of patients whose heart condition is known, usually by direct medical examination. The index patterns of different diseases have different index sequences. Once the best match between the measured integrated pattern 82 and one of the stored patterns is obtained, a diagnosis 110 is made.

As previously mentioned, the test procedure lasts for an extended time period of multiple wave cycles. In the case of a cardiac patient, fifteen sets of data are collected, each over a ten second time interval. The resultant 150-second time period has been found to be sufficient from which to extract reliable data.

FIG. 19 depicts a technique for optimizing the suggested diagnoses. For example, the patient's age data 90 is entered by keyboard entry 12 and, in accordance with Tables I—I set forth below, as represented by block 150, the raw scores are processed in block 152 to obtain so-called "weighted scores". The two highest weighted scores constitute the optimized diagnoses 110 which are sent to the printer/monitor 14, 16 for review by the physician.

TABLE I

| Age | Stroke Weighting Factor ± 5% |
|---|---|
| <25 | 1.0 |
| 25–46 | 1.1 |

TABLE I-continued

| Age | Stroke Weighting Factor ± 5% |
|---|---|
| >46 | 1.5 |

TABLE II

| Age | Epilepsy Weighting Factor ± 5% |
|---|---|
| <25 | 1.0 |
| 25–46 | 1.01 |
| >46 | 1.03 |

Figure 4:
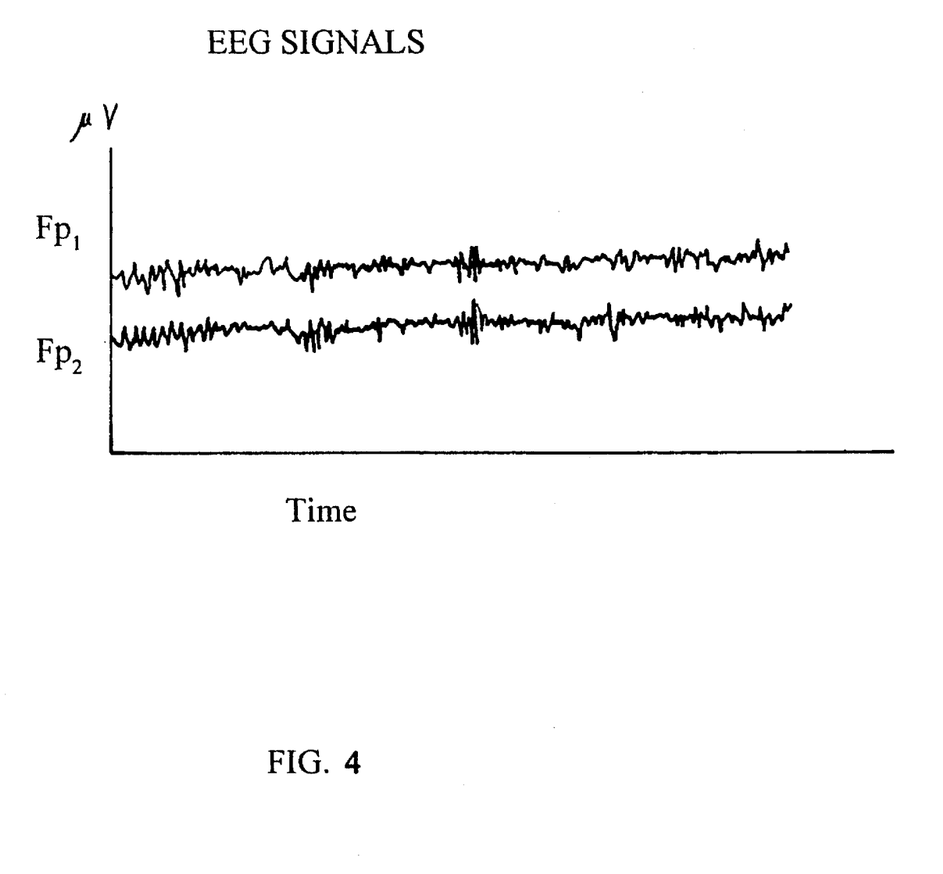
FIG. 4 is a graph of an EEG signal wherein amplitude is plotted against time.

The arrangement 10 can be used to diagnose brain disease. As depicted in FIG. 15, the hook-up to the patient employs a two-wire cable set 112. Each wire has a surface electrode placed at the left and right frontal areas of the brain on the skull of the patient. These are conventionally designated as the "$F_{p1}$ and $F_{p2}$ leads". A representative $F_{p1}$ or $F_{p2}$ signal is shown in FIG. 4 wherein amplitude is plotted against time.

The electrodes produce two analog electrical EEG signals, as represented by block 114, which are fed directly into the analog-to-digital converter 40. The signals are sampled and digitized within the converter. The digital EEG signals are then conducted to the signal processor 42 whereupon, after processing, the data may be displayed on the monitor 14 or printed by the printer 116.

The overall EEG signal processing is depicted in FIG. 3. Transfer function 43 rather than phase angle 46 is determined. Otherwise the functions 43–54 are determined as before. For example, a representative power spectrum characteristic is depicted in FIG. 5 wherein power is plotted against frequency. As also shown in FIG. 5, the delta, theta, alpha and beta frequency bands are indicated. In addition, the aforementioned transfer function 43 is mathematically determined. For example, the pre-set indices for each function are:

(1) HW− Is the highest peak of the power spectrum in the delta band above a limit?
(2) OH—Is the highest peak of the power spectrum in the theta band above a limit?
(3) As−—Is the main peak of the power spectrum of the alpha wave shifted on the theta band?
(4) As+—Is the main peak of the power spectrum of the alpha wave shifted on the beta band?
(5) EV—Is the transfer function curve too even in the low frequency range?
(6) RC—Is the highest peak of the coherence in the theta band higher than that in the alpha band?
(7) RT—Is the highest peak of the transfer function in the theta band higher than that in the alpha band?
(8) PA—Does the shape of the phase angle wave resemble the letter "W"?
(9) LF—Is there a late fluctuation of the impulse response?
(10) L3—Is there a delay of the third peak of the impulse response?
(11) F/A—Is the ration of the occurrence frequency/amplitude of the amplitude histogram above a limit?

As before, once the states of the various indices are recognized, an integrated pattern 140 is generated and statistically matched in a matching program 142 to which a massive data bank 144 of known brain disease patterns is connected. A suggested brain disease 146 is then generated.

Rather than, or in addition to, using age as a weighting factor, other parameters, such as critical information descriptive of the patient, can be employed. For example, if the patient had a known cardiac condition, as verified by actual medical testing, prior to undergoing the diagnosis procedure described herein, that specific medical data 90 is entered, again by keyboard entry (see FIG. 20), whereupon a weighting factor (block 150) is retrieved from memory. This weighting factor, e.g., 1.5±5% is multiplied by the raw score for that specific cardiac condition, virtually insuring that that specific cardiac condition will be one of the two highest weighted scores to be output to the monitor/printer.

In a modification to the last-mentioned procedure, the weighting factor processing can be eliminated, and the specific cardiac condition can be automatically output to the monitor/printer.

Figure 1:
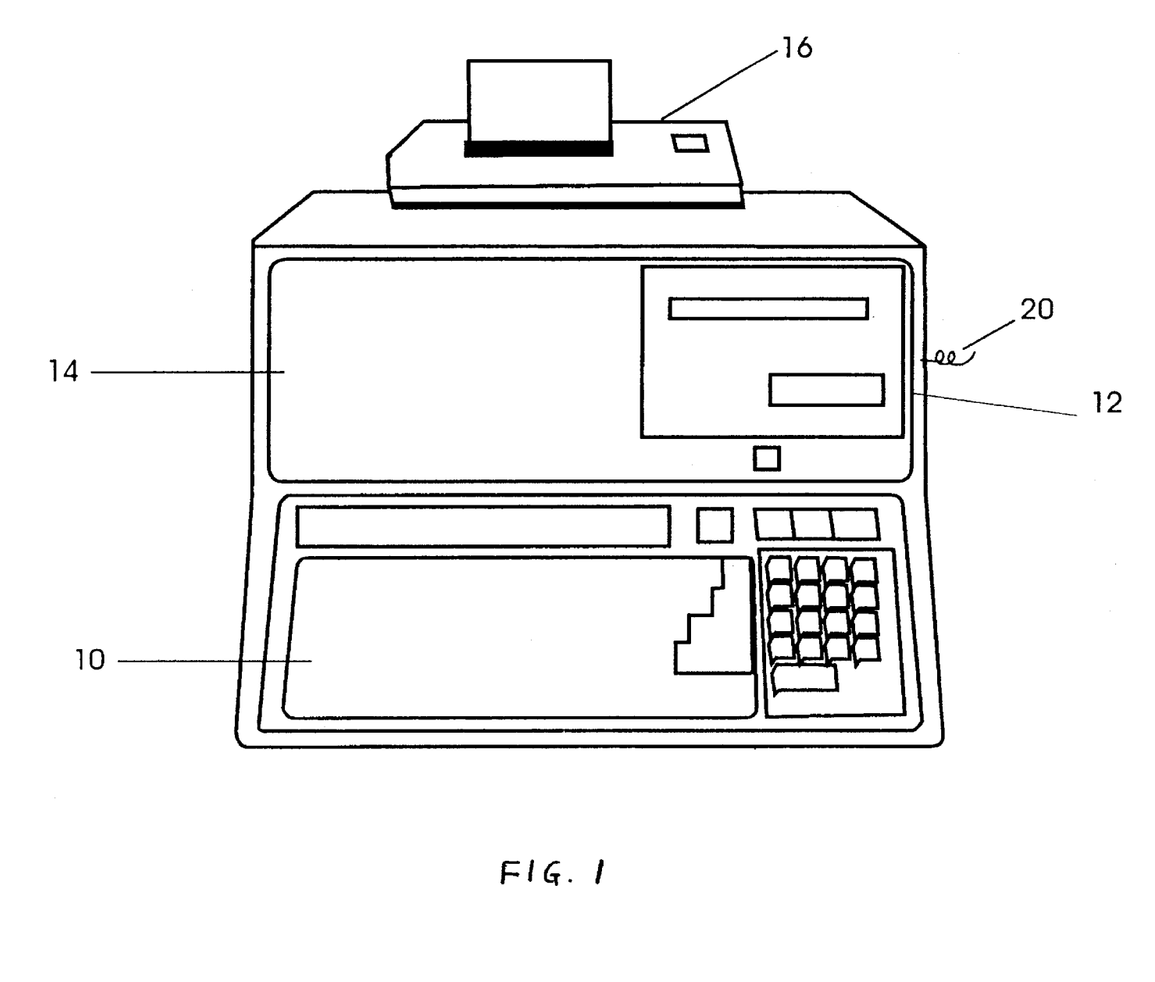
FIG. 1 is a front view of an arrangement in accordance with the method of this invention.
Figure 2:
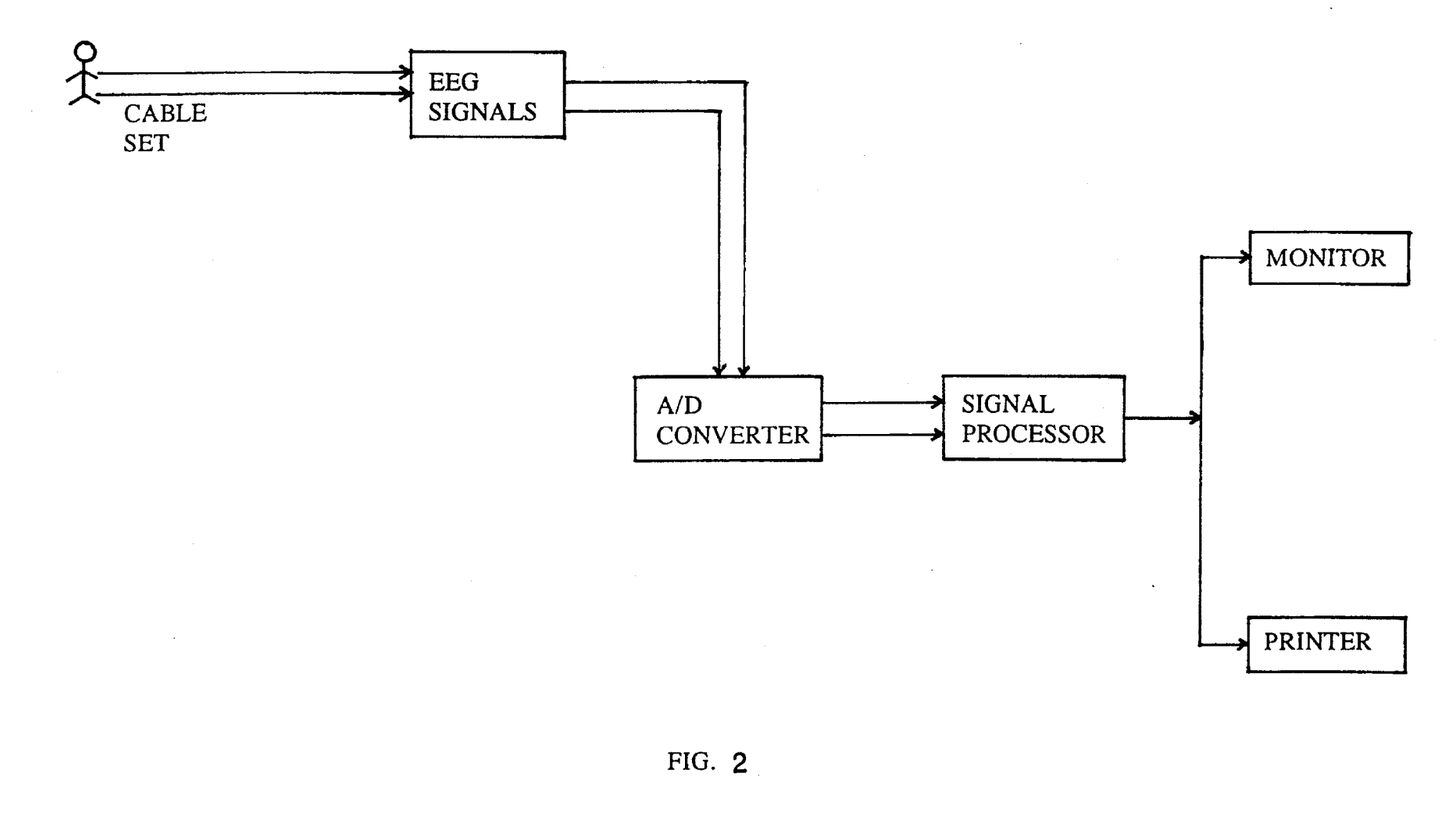
FIG. 2 is a block diagram of the arrangement of FIG. 1 connected to a patient.

FIG. 21 is similar to FIG. 4, except that the illustrated system is now provided with remote transmission and reception of various signals. Rather than being in a physician's office where the arrangement of FIG. 1 is physically located, the patient can be located at home or at remote site 154 where the EKG signals 32 are sent to a transceiver 158. The arrangement of FIG. 1 is located at the physician's office 156 and/or diagnosis center, where another transceiver 160 is located to receive data transmitted by transceiver 158. The transceivers 158, 160 can be a telephone line, either land-based and/or cellular, or can be a radio signal link or, in short, any bidirectional bus. Hence, the FIG. 21 system allows off-site patient testing. The transceivers can transmit or receive analog or digital data.

The signal processor 42 of the FIG. 21 system also generates a warning signal for transmission to transceiver 160 and, in turn, to transceiver 158 and the patient in the event that the current test data exceeds pre-established limits for that patient. As shown in FIG. 22, the patient's previous test data is stored in memory (block 162), and the patient's current test data is stored in block 164. As determined in comparator block 166, if the current data is out-side the pre-established limits for that patient, a warning signal is generated. Otherwise, no warning signal is generated.. This warning signal is used to warn the patient of the presence of a medical emergency.

It will be understood that each of the elements described above, or two or more together, also may find a useful application in other types of constructions differing from the types described above.

While the invention has been illustrated and described as embodied in a method of and arrangement for optimizing disease diagnosis, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention and, therefore, such adaptations should and are intended to be comprehended within the meaning and range of equivalence of the following claims.

What is claimed as new and desired to be protected by Letters Patent is set forth in the appended claims.

I claim:

1. A method of optimizing the diagnosis of a condition of a patient tested, comprising the steps of:

(a) acquiring electroencephalogram (analog signals) from the patient;

(b) mathematically determining a plurality of functions descriptive of the patient from the signals;

(c) establishing a set of indices for each function, each index having two states, each indicative of the condition of the patient;

(d) recognizing the state of each index for each function;

(e) generating an integrated pattern of the states of the indices from a plurality of the functions;

(f) storing a collection of index patterns, each containing a multitude of patterns of the states of indices for a multitude of patients whose condition is known;

(g) matching the generated integrated pattern against the stored collection of index patterns to obtain a plurality of raw scores;

(h) inputting the critical diagnostic factors, which effect the diagnosis of brain diseases into the device;

(i) establishing a set of weights for each of the critical diagnostic factors which effect the diagnosis of brain diseases, according to the importance of such factors;

(j) weighting the raw scores to obtain weighted scores; and (k) presenting an optimized diagnosis based on the weighted scores.

2. An arrangement for optimizing the diagnosis of a condition of a patient tested, comprising:

(a) means for acquiring electroencephalogram (analog signals) from the patient;

(b) means for mathematically determining a plurality of functions descriptive of the patent from the signals;

(c) means for establishing a set of indices for each function, each index having two states, each indicative of the condition of the patient;

(d) means for recognizing the state of each index for each function;

(e) means for generating an integrated pattern of the states of the indices from a plurality of the functions;

(f) means for storing a collection of index patterns, each containing a multitude of patterns of the states of indices for a multitude of patients whose condition is known;

(g) means for matching the generated integrated pattern against the stored collection of index patterns to obtain a plurality of raw scores;

(h) means for weighting the raw scores to obtain weighted scores;

(i) means for presenting an optimized diagnosis based on the weighted scores;

(j) said establishing indices including:

(1) HW—Is the highest peak of the power spectrum in the delta band above a limit as well as too wide?

(2) OH—Is the highest peak of the power spectrum in the theta band above a limit?

(3) As——Is the main peak of the power spectrum of the alpha wave shifted to the theta band?

(4) As+——Is the main peak of the power spectrum of the alpha wave shifted to the beta band?

(5) EV—Is the transfer function curve too even in the low frequency range?

(6) RC—Is the highest peak of the coherence in the theta band higher than that in the alpha band?

(7) RT—Is the highest meek of the transfer function in the theta band higher than that in the alpha band?

(8) PA—Does the shape of the phase angle wave resemble the letter "W"?

(9) LF—Is there a late fluctuation of the impulse response?

(10) L3—Is there a delay of the third peak of the impulse response?

(11) F/A—Is the ratio of the occurrence frequency/amplitude of the amplitude histogram above a limit?

* * * * *